United States Patent
Chae

(10) Patent No.: US 10,860,097 B2
(45) Date of Patent: *Dec. 8, 2020

(54) EYE-BRAIN INTERFACE (EBI) SYSTEM AND METHOD FOR CONTROLLING SAME

(71) Applicant: Looxid Labs, Inc., Daejeon (KR)

(72) Inventor: Yongwook Chae, Seoul (KR)

(73) Assignee: Looxid Labs, Inc., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/601,418

(22) Filed: Oct. 14, 2019

(65) Prior Publication Data

US 2020/0057495 A1 Feb. 20, 2020

Related U.S. Application Data

(63) Continuation of application No. 15/740,298, filed as application No. PCT/KR2015/013894 on Dec. 17, 2015, now Pat. No. 10,481,683.

(51) Int. Cl.
*G06F 3/01* (2006.01)
*G06F 1/16* (2006.01)
(Continued)

(52) U.S. Cl.
CPC ............ *G06F 3/013* (2013.01); *A61B 5/16* (2013.01); *G06F 1/163* (2013.01); *G06F 3/011* (2013.01);
(Continued)

(58) Field of Classification Search
CPC ....... A61B 5/0476; G06F 3/011; G06F 3/013; G06F 3/015; G06F 3/0484; G06K 9/20; G06T 7/20
See application file for complete search history.

(56) References Cited

U.S. PATENT DOCUMENTS

2012/0257035 A1* 10/2012 Larsen ............... G06F 3/017
348/78
2013/0307771 A1 11/2013 Parker et al.
(Continued)

FOREIGN PATENT DOCUMENTS

EP 2685351 A1 1/2014
JP 2004-152046 5/2004
(Continued)

OTHER PUBLICATIONS

International Search Report, for International Patent Application No. PCT/KR2015/013894, dated Sep. 1, 2016 (in Korean).
(Continued)

*Primary Examiner* — Nelson M Rosario
(74) *Attorney, Agent, or Firm* — Weaver Austin Villeneuve & Sampson LLP

(57) ABSTRACT

Methods and systems for calibrating an eye-brain interface (EBI) system controlled on the basis of eye movements and brain waves according to one embodiment of the present invention are disclosed. A method includes: providing an eye-brain calibration (EBC) interface for calibrating eye movements and brain waves simultaneously, wherein the EBC interface includes a visual object and instructs a user to gaze into the visual object in a particular cognitive state; acquiring eye movements and brain waves of the user for the visual object included in the EBC interface; mapping the visual object and eye movements of the user; and mapping the particular cognitive state instructed to the user and brain waves of the user.

11 Claims, 12 Drawing Sheets

(51) Int. Cl.
  *G06F 3/0484* (2013.01)
  *A61B 5/16* (2006.01)
  *G06F 3/0487* (2013.01)
  *A61B 5/00* (2006.01)

(52) U.S. Cl.
  CPC .............. *G06F 3/015* (2013.01); *G06F 3/017* (2013.01); *G06F 3/0487* (2013.01); *G06F 3/04842* (2013.01); *A61B 5/0024* (2013.01); *G06F 2203/0381* (2013.01)

(56) References Cited

U.S. PATENT DOCUMENTS

| | | |
|---|---|---|
| 2014/0022157 A1 | 1/2014 | Lee |
| 2014/0347265 A1 | 11/2014 | Amone et al. |
| 2015/0271478 A1 | 9/2015 | Zhou |
| 2016/0210407 A1 | 7/2016 | Hwang |
| 2018/0146183 A1 | 5/2018 | Zhou |
| 2018/0196511 A1 | 7/2018 | Chae |

FOREIGN PATENT DOCUMENTS

| | | |
|---|---|---|
| JP | 2006/136464 | 6/2006 |
| JP | 2007/025963 | 2/2007 |
| JP | 2012/221498 | 11/2012 |
| KR | 10-2012-0124772 A | 11/2012 |
| KR | 10-2013-0015488 A | 2/2013 |
| WO | WO 2008-056492 | 5/2008 |
| WO | WO 2008/059878 | 5/2008 |
| WO | WO 2012/133185 | 10/2012 |
| WO | WO 2015/047032 | 4/2015 |
| WO | WO2017/104869 | 6/2017 |

OTHER PUBLICATIONS

"*Proposal of a control system based on mood extraction*", The 6th Forum on Data Engineering and Information Management, Japan, Institute of Electronics, Information and Technology, Technical Commission, Japan Research Institute of Japan Database Society, May 30, 2014. [with machine translation].

"Research on Brain Machine Interface—Identification of vertical movement using brain waves", The 31st Annual Conference of the Robotics Society of Japan, Dec. 20, 2013. [with machine translation].

Notice of Reasons for Refusal, dated Jun. 17, 2019, for Japanese Patent Application No. 2018-551726, with English Translation.

Extended European Search Report, dated Jul. 30, 2019, for European Patent Application No. 159107929.9, 16 pages.

Non-Final Rejection, dated Apr. 1, 2019, for U.S. Appl. No. 15/740,298.

Notice of Allowance and Fees Due (PTOL-85), dated Jul. 15, 2019, for U.S. Appl. No. 15/740,298.

* cited by examiner

Fig. 4A
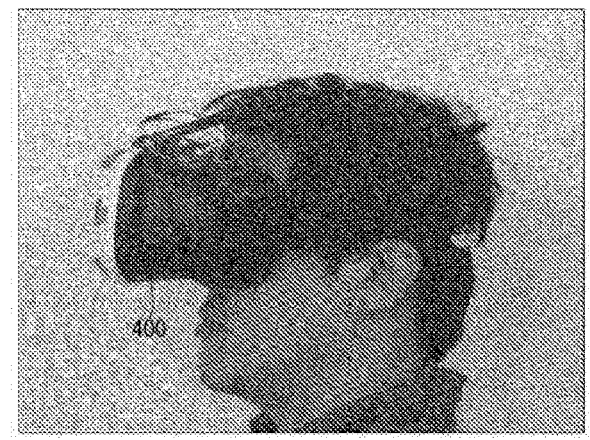
Fig. 4B
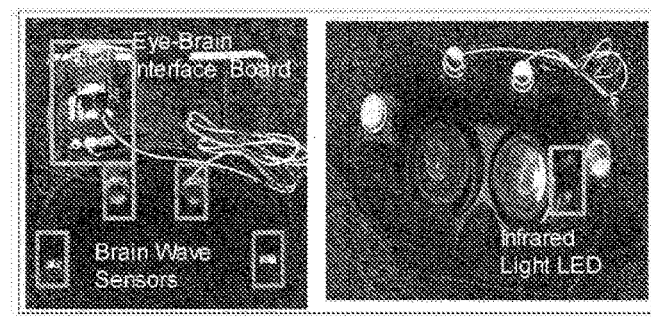
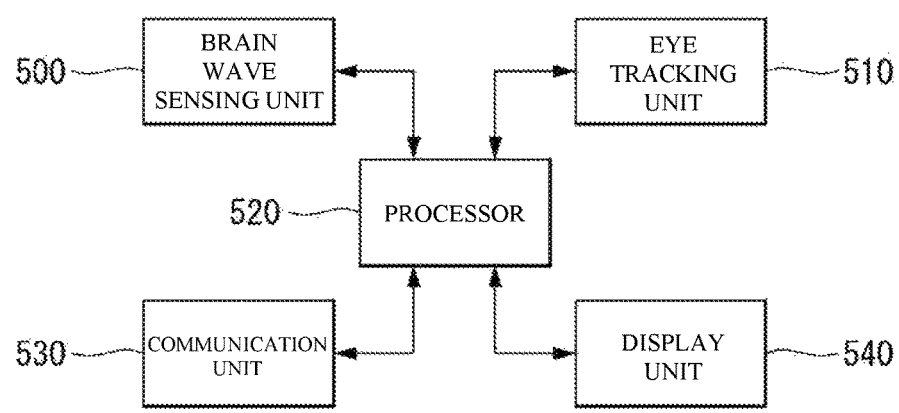
FIG. 5

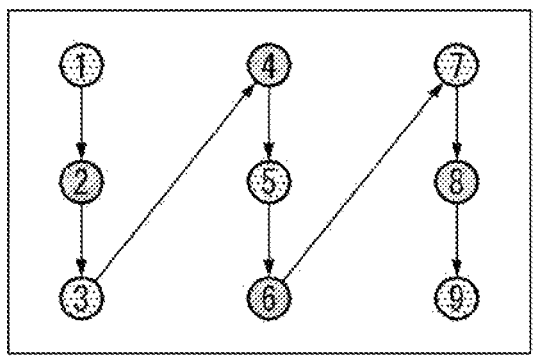
Fig. 6A
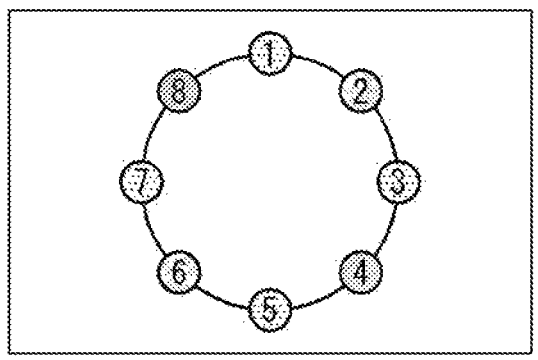
Fig. 6B
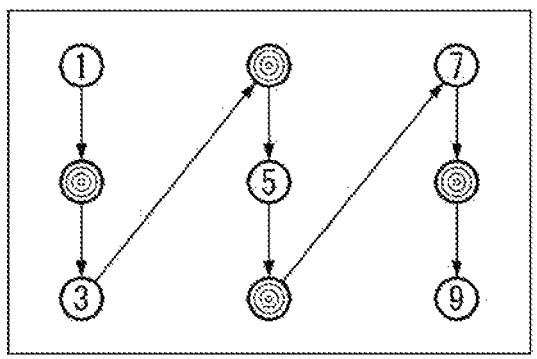
Fig. 6C
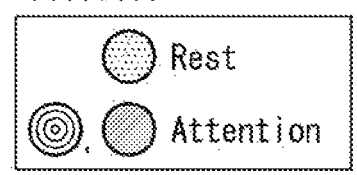

EYE-BRAIN INTERFACE (EBI) SYSTEM AND METHOD FOR CONTROLLING SAME

TECHNICAL FIELD

The present disclosure relates to an eye-brain interface (EBI) system controlled by a user's brain waves and eye tracking, and a method for controlling the same. More specifically, the present disclosure relates to a method for calibrating an EBI system.

BACKGROUND ART

The brain is an organ of the central nervous system that is responsible for obtaining and processing of stimuli. It is responsible for not only mental activities such as memory and judgment as well as physical activities and emotional reactions. In particular, the frontal lobe is located at the front of the cerebrum and is responsible for the movement of the body according to thinking, planning and judging. The frontal lobe has Broca area that is a group of neurons performing important functions, and accordingly it can perform more complex functions than other cerebral parts. In addition, the prefrontal lobe, which is the widest part of the frontal lobe, is a region that distinguishes humans from other animals. It is known that the prefrontal lobe synthesizes sensory information and induce high-level mental activities. As the significance of the frontal lobe has become increasingly appreciated, research is ongoing on basic brain science related to the functions, diseases and disorders of the frontal lobe. In addition, treatment using brain waves extracted from the frontal lobe, brain fitness, and brain-computer interface (BCI) technology are being developed.

The BCI technology was first mentioned in 1973 at the UCLA Lab. Until the mid-2000s, however, it was in the stage of R&D and test application. However, with the launch of a variety of headset type brain wave measurement devices such as EPOC from Emotiv, Muse from Interexon and MindWave from NeuroSky, BCI is also rapidly developing and put into practical use.

SUMMARY OF INVENTION

Technical Problem

It is an object of the present disclosure to provide a method for calibrating brain waves and eye tracking simultaneously in an EBI system.

It is another object of the present disclosure to provide a method for calibrating brain waves and eye tracking more accurately and efficiently in an EBI system.

It is an object of the present disclosure to provide a method for obtaining an iris pattern in a process of calibrating eye tracking.

It is an object of the present disclosure to provide a method for re-calibrating brain waves and eye tracking by measuring a user's emotional index.

It is yet another object of the present disclosure to provide a method for controlling an EBI system based on a user's brain wave and eye tracking based on a result of calibration.

Solution to Problem

According to an aspect of the present disclosure, a method for calibrating an eye-brain interface (EBI) system, which is controlled based on eye tracking and brain waves, includes: providing an eye-brain calibration (EBC) interface for calibrating the eye tracking and brain waves together, wherein the EBC interface comprises a visual object and instructs a user to gaze the visual object in a particular cognitive state; obtaining the user's gaze position and brain wave on the visual object included in the EBC interface; mapping the visual object with the user's gaze position; and mapping the particular cognitive state with the user's brain wave.

The mapping the user's gaze position may include mapping coordinates of the visual object on a screen with coordinates of the user's gaze position.

The EBC interface may sequentially and/or alternately provide a first visual object indicating a first cognitive state and a second visual object indicating a second cognitive state.

The first cognitive state may be a cognitive state of attention and/or selection, and the second cognitive state may be a cognitive state of rest and/or search.

The mapping the user's brain wave may include: obtaining first raw data on a brain wave in the first cognitive state, and second raw data on a brain wave in the second cognitive state; converting frequencies of the first raw data and the second raw data; and setting a criterion for classifying the first and second cognitive states based on the frequency characteristics of the frequency-converted first raw data and the second raw data.

The setting the criterion may include: extracting a frequency amplitude for each of frequency bands in a predetermined range from the frequency-converted first raw data and second raw data; obtaining a Fisher's ratio for each of the frequency bands using the extracted frequency amplitude; selecting a first frequency band having a highest Fisher's ratio and a second frequency band having a second highest Fisher's ratio; and setting the first and second frequency bands as the criteria for classifying the first and second cognitive states.

The Fisher's ratio may be calculated based on an average and a variance of the frequency amplitudes in the frequency-converted first raw data and an average and a variance of the frequency amplitudes in the frequency-converted second raw data.

The frequency band in the predetermined range may correspond to $\delta$-wave band, $\theta$-wave band, $\alpha$-wave band or $\beta$-wave band of a brain wave.

The EBC interface may adjust a flickering frequency of the visual object to thereby induce the user's brain wave to a particular frequency band.

The EBC interface may adjust the flickering frequency of the visual object to approximately 8 to 13 Hz to induce the user's brain wave to an alpha wave range, and adjust the flickering frequency of the visual object to approximately 13 to 30 Hz to induce the user's brain wave to a beta wave range.

The method may further include: obtaining an iris image from the user's eye; and coding the iris image.

The coding the iris image may include: dividing the obtained iris image into a plurality of images; arranging the plurality of images in one direction; and converting the images arranged in the one direction into a single two-dimensional image.

According to another aspect of the present disclosure, a slave device for measuring gaze position and brain waves includes: an eye tracking unit configured to track a user's eye; a brain wave sensing unit configured to sense the user's brain wave; a communication unit configured to conduct communications with a host device; and a processor configured to control the eye tracking unit, the brain wave sensing unit and the communication unit. The host device provides an eye-brain calibration (EBC) interface for simultaneously calibrating eye tracking and brain waves. The EBC interface includes a visual object and instructs the user to gaze at the visual object in a particular cognitive state. The processor, upon receiving a calibration start signal from the host device, obtains the user's gaze position and brain wave together and transmits the user's gaze position and the brain wave to the host device.

According to yet another aspect of the present disclosure, a host device controlled based on eye tracking and brain waves includes: a display unit configured to display an image; a communication unit configured to conduct communications with a slave device; and a processor configured to control the display unit and the communication unit. The processor provides an eye-brain calibration (EBC) interface for simultaneously calibrating eye tracking and brain waves. The EBC interface includes a visual object and instructs the user to gaze at the visual object in a particular cognitive state. The processor requests and receives the user's gaze position and brain waves from the slave device, maps the visual object with the user's gaze position, and maps the user's brain wave with the particular cognitive state.

The processor may map coordinates of the visual object on a screen with coordinates of the user's gaze position when it maps the user's gaze position.

The EBC interface may sequentially and/or alternately provide a first visual object indicating a first cognitive state and a second visual object indicating a second cognitive state.

The first cognitive state may be a cognitive state of attention or selection, and the second cognitive state may be a cognitive state of rest or search.

The processor, when it maps the user's brain wave, may obtain first raw data on a brain wave in the first cognitive state, and second raw data on a brain wave in the second cognitive state, convert frequencies of the first raw data and the second raw data, and extract a frequency amplitude for each of frequency bands in a predetermined range from the frequency-converted first raw data and second raw data, obtain a Fisher's ratio for each of the frequency bands using the extracted frequency amplitude, select a first frequency band having a highest Fisher's ratio and a second frequency band having a second highest Fisher's ratio, and set the first and second frequency bands as the criteria for classifying the first and second cognitive states.

The processor may obtain the user's brain waves in real-time and classify the user's brain waves obtained in real-time according to the classification criterion in real-time.

The EBC interface may adjust a flickering frequency of the visual object to thereby induce the user's brain wave to a particular frequency band.

Advantageous Effects

According to an exemplary embodiment of the present disclosure, there is provided an EBC interface capable of simultaneously calibrating the brain waves and the eye tracking, so that a user can more easily and quickly calibrate the brain waves and the eye tracking simultaneously.

According to another exemplary embodiment of the present disclosure, cognitive states of brain waves are classified using the frequency characteristic of the brain waves, so that the cognitive states of the brain waves can be more accurately distinguished.

According to another exemplary embodiment of the present disclosure, an iris pattern can be utilized as user authentication information.

According to another exemplary embodiment of the present disclosure, a user's brain wave and gaze position can be accurately mapped/classified as a result of calibration, so that an EBI system can be provided that operates as intended by the user.

In addition to those described above, other various effects of the present disclosure will be described in detail below with reference to the drawings.

BRIEF DESCRIPTION OF DRAWINGS

FIGS. 4A and 4B are diagrams illustrating an eye-brain (EBI) device according to an exemplary embodiment of the present disclosure.

FIG. 5 is a block diagram of the EBI device according to an exemplary embodiment of the present disclosure.

FIGS. 6A to 6C are diagrams illustrating exemplary embodiments of the EBC interface.

BEST MODES FOR CARRYING OUT THE INVENTION

The terms used herein are ordinary and currently widely used terms in the art in consideration of functions in regard to the inventive concept. However, the terms may be changed depending on the intention of those of ordinary skill in the art, precedents, or appearance of new technology. Some terms are arbitrarily selected by the applicant, and in such case, the detailed meaning thereof will be described in the detailed description. Thus, the terms used herein should be understood not based on nominal names but on the substantial meaning of the terms within the context.

Hereinafter, exemplary embodiments of the present disclosure will be described in detail with reference to the accompanying drawings. However, the present disclosure is not limited to these exemplary embodiments.

Hereinafter, exemplary embodiments of the present disclosure will be described in more detail with reference to the accompanying drawings.

Figure 1:
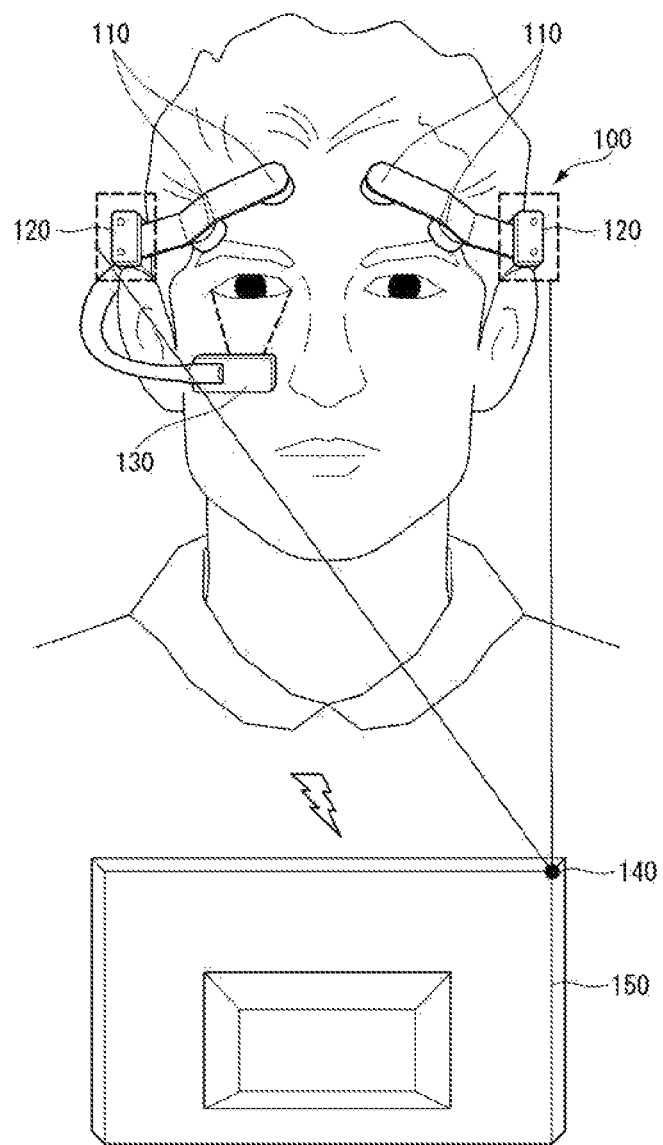
FIG. 1 is a diagram illustrating an eye-brain interface system according to an exemplary embodiment of the present disclosure.
Figure 2:
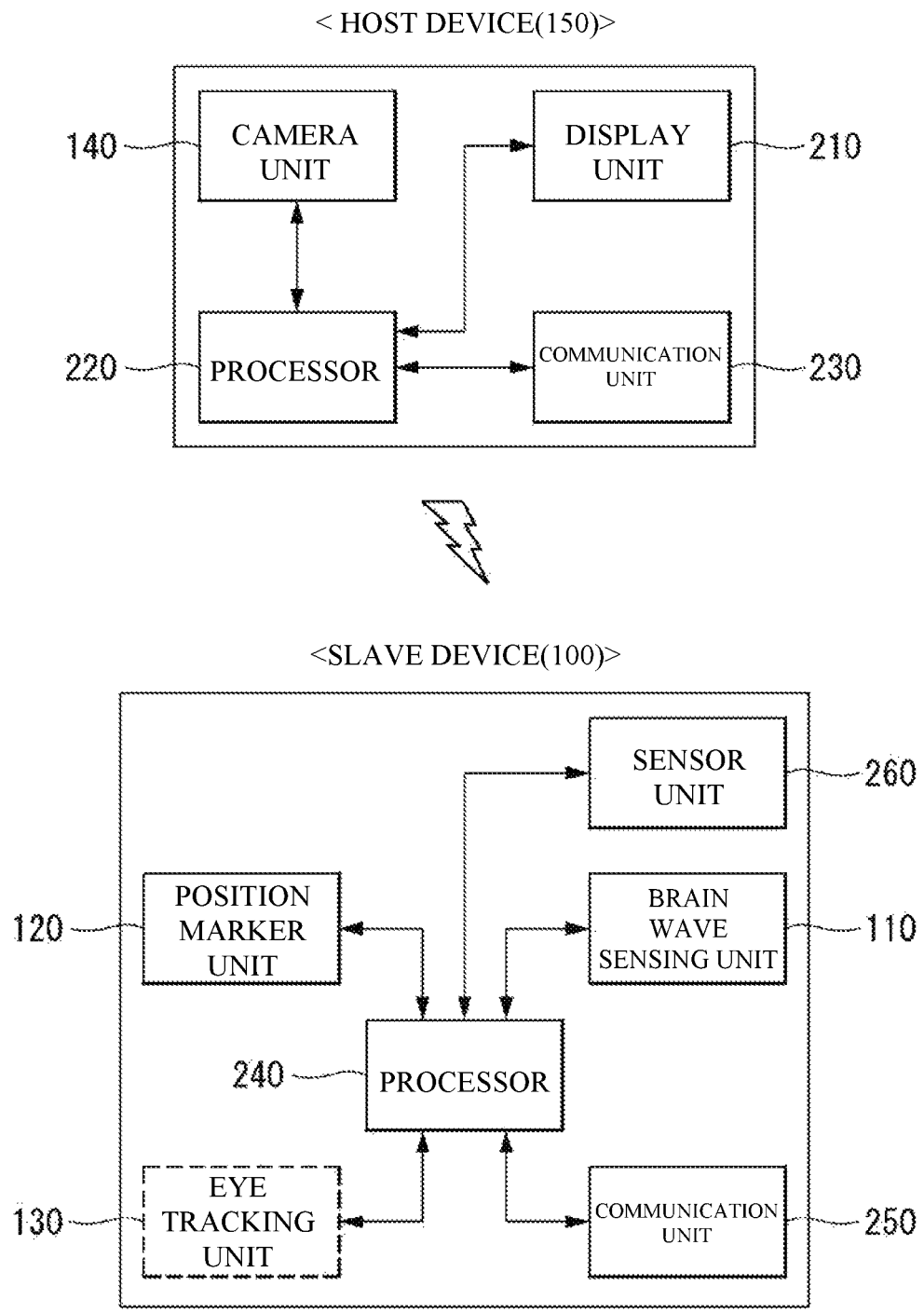
FIG. 2 is a block diagram of a host device and a slave device according to an exemplary embodiment of the present disclosure.

FIG. 1 is a diagram illustrating an eye-brain interface system according to an exemplary embodiment of the present disclosure. FIG. 2 is a block diagram of a host device and a slave device according to the exemplary embodiment of the present disclosure.

Referring to FIG. 1, an eye-brain interface (EBI) system according to the exemplary embodiment of the present disclosure may include a host device 150 and a slave device 100.

The slave device 100 may include a variety of types of wearable devices that can be worn by a user. For example, the slave device 100 may be a device that is in contact with/worn on a part of a user's body, such as a head-mounted display (HMD), a headset, a smart ring, a smart watch, an earset and ear phones. The slave device 100 may include at least one sensor to sense a user's bio-signals from a part of the user's body. As used herein, the bio-signals may refer to a variety of signals generated from a user's body in accordance with the user's conscious and/or unconscious behaviors (e.g., breathing, heartbeat, metabolism, etc.) such as pulse, blood pressure and brain waves. In particular, the slave device 100 according to the exemplary embodiment of the present disclosure may sense a user's brain waves as the user's bio-signals and transmit the sensing results to the host device 150.

The host device 150 may refer to a device that operates based on the results of sensing the bio-signals received from the slave device 100. More specifically, the host device 150 may include a variety of electronic devices that receive the results of sensing the user's bio-signals from the slave device 100 and perform various operations based on the received results. The host device 150 may include a variety of electronic devices such as a TV, a smart phone, a tablet PC, a smart car, a PC and a laptop computer.

The EBI system includes the slave device 100 and the host device 150 and is controlled based on a user's bio-signals. Therefore, even if the user does not perform a separate input intended for the system, the system can determine the user's intention by sensing the user's bio-signals and is controlled accordingly. As a result, the EBI system is controlled more conveniently and accurately by the user. Hereinafter, the configuration of the slave device 100 and the host device 150 will be described in more detail.

Referring to FIGS. 1 and 2, the slave device 100 may include a position marker unit 120, an eye tracking unit 130, a brain wave sensing unit 110, a sensor unit 260, a communication unit 250, and a processor 240.

The position marker unit 120 may include at least one light-emitting element for emitting light (for example, an infrared LED). The host device 150 may track the position marker unit of the slave device 100 in real-time so that the location and position of the user wearing the slave device 100, the distance between the host device 150 and the user, and the relative location (hereinafter referred to as "user's position") may be detected.

When the position marker unit 120 includes a plurality of light-emitting elements, the plurality of light-emitting elements may be located in the position marker unit 120 such that they are spaced apart from one another by a predetermined distance. In this case, the host device 150 may track the light-emitting elements of each position marker unit 120 and measure the distance between the light-emitting elements in real-time, to thereby detect the relative distance between the host device 150 and the user. For example, when the position marker unit 120 moves away from the host device 150, the distance between the light-emitting elements measured by the host device 150 may decrease, and when the position marker unit 120 moves toward the host device 150, the distance between the light-emitting elements measured by the host device 150 may increase. Based on this, the host device 150 may calculate the ratio between the distance between the light-emitting elements measured in real-time and the predetermined actual distance between the light-emitting elements, thereby calculating the relative distance between the host device 150 and the user.

The position marker unit 120 for tracking the position of the user may be included in the slave device 100 in various forms. The host device 150 may detect the position of the user based on the number and size of the position marker units 120, the number, position and spacing distance of light-emitting elements included in the position marker units 120, etc.

The eye tracking unit 130 may track the user's gaze position. The eye tracking unit 130 may be mounted in the slave device 100 such that it is located around the user's eye to track the user's gaze position (eye movement) in real-time.

The eye tracking unit 130 may include a light-emitting element (for example, an infrared LED) that emits light and a camera sensor that receives (or senses) light emitted from the light-emitting element. The eye tracking unit 130 may capture the light reflected off the user's eyes with the camera sensor and transmit the captured image to the processor 240 (video analysis technique). In the following description, the video analysis technique is employed by the eye tracking unit 130 for convenience of illustration. It is, however, to be understood that this is merely illustrative. The eye tracking unit 130 may track the user's eye by employing a contact lens technique (eye tracking scheme using the light reflected off a mirror embedded in a contact lens or using magnetic field of a coil embedded in a contact lens) or a sensor attaching technique (eye tracking scheme using an electric field according to the movement of the eyes by attaching sensors around the eyes).

The brain wave sensing unit 110 may sense a user's brain waves. The brain wave sensing unit 110 may include at least one EEG (Electroencephalogram) sensor, MEG (magnetoencephalography) sensor, and/or NIRS (Near-Infrared Spectrometer). The brain wave sensing unit 110 may be mounted on the slave device 100 such that it is in contact with a part of a user's body (e.g., head) from which the user's brain wave can be measured when the user wears the slave device 100, thereby measuring the user's brain wave. The brain wave sensing unit 110 measures electrical/optical frequencies that vary depending on brain waves of a variety of frequencies generated from a part of the user's body in contact with it or activation states of the brain.

Since the brain waves are bio-signals, different users have different brain waves. Therefore, different patterns of brain waves may be extracted from different users even the users are in the same cognitive state (for example, attention/non-attention/selection/search, etc.). As a result, it is not accurate enough to determine a user's current cognitive state by simply extracting the user's brain wave and analyzing it based on a single criterion. Therefore, in order to accurately measure a user's cognitive state based on the brain waves, according to the exemplary embodiment of the present disclosure, a method for calibrating brain waves according to the cognitive state of each user. A more detailed description thereof will be given below with reference to FIGS. 11 to 14.

The sensor unit 260 may include at least one sensing means and may use it to sense the environment of the device 100. Further, the sensor unit 260 may transmit the sensing results to the processor. In particular, the sensor unit according to the exemplary embodiment of the present disclosure may sense the motion, movement and the like of the slave device 100 and may transmit the sensing results to the processor 240.

The sensor unit 260 may include, as sensing means, an inertia measurement unit (IMU) sensor, a gravity sensor, a geomagnetic sensor, a motion sensor, a gyro sensor, an accelerometer, a magnetometer, an acceleration sensor, an infrared sensor, an inclination sensor, an altitude sensor, an illuminance sensor, a global positioning system (GPS) sensor, and the like. The sensor unit 260 collectively refers to various sensing means described above, and may sense the various inputs from a user and the environment of the device to transmit the sensing results so that the processor can perform operation accordingly. The above-described sensing means may be included in the slave device 100 as a separate element or may be incorporated into at least one element.

The communication unit 250 may conduct communications with an external device using various protocols and may transmit/receive data through the communications. The communication unit 250 may be connected to a network in a wired or wireless manner, and may transmit/receive various signals and/or data. The slave device 100 may perform pairing with the host device 150 using the communication unit 250. In addition, the slave device 100 may transmit/receive various signals/data to/from the host device 150 using the communication unit 250.

The processor 240 may control the position marker unit 120, the eye tracking unit 130, the brain wave sensing unit 110, the sensor unit 260, and the communication unit 250. The processor 240 may control transmission/reception of signals (or data) among the above-described units.

In particular, the processor 240 according to the exemplary embodiment of the present disclosure may transmit sensing results received from at least one sensor included in the slave device 100 to the host device 150. As used herein, the sensing results may refer to raw data obtained by using at least one sensor included in the slave device 100 or data obtained by processing raw data with a predetermined algorithm.

In addition, the processor 240 may perform various operations for calibrating a user's gaze position and brain waves, which will be described later in detail with reference to FIGS. 6 to 13.

In the foregoing description, the constituent units included in the slave device 100 according to the exemplary embodiment of the present disclosure have been described. The slave device 100 may optionally include some of the constituent units shown in FIGS. 1 and 2. In addition, the slave device 100 may further include various units required for the use and operation of the device, such as a memory unit, a camera unit and a power supply unit.

The host device 150 may include a camera unit 140, a display unit 210, a communication unit 230, and a processor 220.

The camera unit 140 may capture the position marker unit 120 of the slave device 100. More specifically, the camera unit 140 may captured the position marker unit 120 of the slave device 100 to obtain a captured image of the position marker unit 120. The camera unit 140 may transmit the obtained image to the processor 220. The processor 220 may process the captured image to obtain the position of the user wearing the slave device 100. In this case, the processor 220 may obtain the position of the user by analyzing the position and size of the position marker units 120, the number, the position and the spacing distance of the included light-emitting elements.

The camera unit 140 may be a wide-angle camera having an angle of view of approximately 60 degrees or more. If the camera unit 140 is implemented with an ordinary camera (a camera having an angle of view of less than 60 degrees), the position of the user can be tracked at a left-to-right angle of approximately 60 degrees in front of the host device 150, and in the range of approximately 60 to 90 cm between the slave device 100 and the host device 150. In contrast, if the camera unit 140 is implemented with a wide-angle camera (a camera having an angle of view of 60 degrees or more), the position of the user can be tracked at a left-to-right angle of approximately 170 degrees in front of the host device 150, and in the range of approximately 3 m between the slave device 100 and the host device 150. Therefore, the camera unit 140 may be implemented with a wide-angle camera to obtain more accurate data on a user's position.

The display unit 210 may display an image thereon. As used herein, the image may refer to a still image, a moving image, a text, a virtual reality (VR) image, an augmented reality (AR) image or a variety of other visual representations including them that can be displayed on the screen. The display unit 210 may include at least one of: a liquid-crystal display, a thin-film transistor liquid-crystal display, an organic light-emitting diode (OLED) display, a 3D display, and a transparent organic light-emitting diode (TOLED) display. In addition, the display unit 210 may be fabricated in the form of a metal foil, a very thin grass, or a plastic substrate. In particular, when it is fabricated in the form of a plastic substrate, a PC substrate, a PET substrate, a PES substrate, a PI substrate, a PEN substrate, an AryLite substrate, etc. may be employed.

The communication unit 230 may conduct communications with an external device using various protocols and may transmit/receive data through the communications. The communication unit 230 may be connected to a network in a wired or wireless manner, and may transmit/receive various signals and/or data. The host device 150 may perform pairing with the slave device 100 using the communication unit 230. In addition, the host device 150 may transmit/receive various signals/data to/from the slave device 150 using the communication unit 230.

The processor 220 may include the camera unit 140, the display unit 210 and the communication unit 230. The processor 220 may control transmission/reception of signals (or data) among the above-described units.

In particular, the processor 220 according to the exemplary embodiment of the present disclosure may execute various commands (or operations) in response to the sensing results received from the slave device 100. For example, when coordinates of a user's gaze position is received as a result of the sensing, the processor 220 may execute a command to select a visual object (e.g., an icon) at a particular location on the display unit 210 mapped with the coordinates. Further, when the user's brain wave data corresponding to "attention" state is received as a result of the sensing, the processor 220 may execute a command to run the selected visual object (e.g., to run the application corresponding to the selected icon).

In doing so, in order to specify the point on the display unit 210 mapped with the coordinates of the user's gaze position received by the processor 220, it is necessary to perform calibration to map the coordinates of the user's gaze position with the coordinates of the points on the display unit 210 in advance. In addition, as mentioned earlier, since different users have different brain wave patterns according to cognitive states, it is also necessary to perform calibration to map the user's cognitive states with brain waves of frequencies in advance. In view of the above, according to an exemplary embodiment of the present disclosure, there is provided an eye-brain calibration (EBC) interface for simultaneously calibrating a user's gaze position and brain waves, which will be described in detail below with reference to FIGS. 6 to 13.

In the foregoing description, the constituent units included in the host device 150 according to the exemplary embodiment of the present disclosure have been described. The host device 150 may optionally include some of the constituent units shown in FIGS. 1 and 2. In addition, the host device 150 may further include various units required for the use and operation of the device, such as a sensor unit, a memory unit and a power supply unit.

Although the units included in the host device 150 and those included in the slave device 100 are shown separately in the block diagrams for the convenience of illustration, the units of the slave device 100 may be included in the host device 150 and vice versa. For example, in other implementations, the eye tracking unit of the slave device 100 may be included in the host device 150.

The processors 220 and 240 may be incorporated in the (slave or host) devices or may be implemented as separate elements external to the devices (not shown). When the processors 220 and 240 are implemented as separated elements (external elements), the processors 220 and 240 may be in the form of external processors that are convenient for a user to carry. In this case, the user may connect the external processors 220 and 240 to a certain device as necessary, and the device may become a slave or host device 100 or 150. In this case, the external processors 220 and 240 may process various data (especially data relating to the user's bio-signals) with a predetermined algorithm so that the device connected thereto can perform the functions of the slave or host device 100 or 150. It is to be noted that in order for the device connected to the external processors 220 and 240 to perform the functions of the slave device 100, the device is required to have a unit capable of sensing the user's bio-signals.

In the following description, the processors and the slave/host devices 100 and 150 may be regarded as the identical element. In addition, in the block diagram shown in FIG. 2 according to the exemplary embodiment of the present disclosure, the blocks represent hardware elements of the slave/host devices 100 and 150 by logically separating them from one another. Thus, the elements of the slave/host devices 100 and 150 described above may be mounted as a single chip or as a plurality of chips, depending on the design of each device.

Figure 3A:
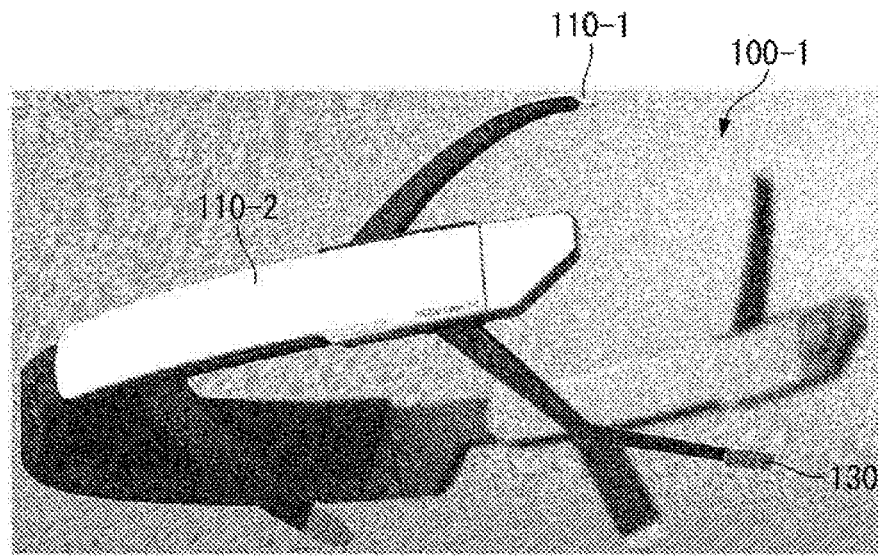
FIGS. 3A and 3B are diagrams illustrating various embodiments of the slave device.
Figure 3B:
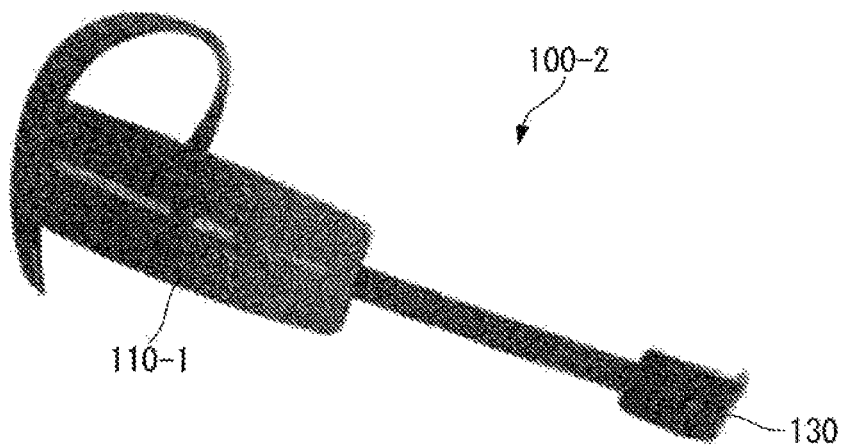

FIGS. 3A and 3B are diagrams illustrating various embodiments of the slave device.

The slave device may be implemented in various form factors.

Referring to FIG. 3A, a slave device 100-1 may be implemented as a headset. A brain wave sensing unit 110-1 of the slave device 100-1 may be located such that it is in contact with a user's head and/or forehead, and may sense the user's brain waves from the head and/or forehead. In addition, an eye tracking unit 130 may be located around the user's eyes and may track the user's eye in real-time. A sensor unit 110-2 may be located in the main body of the slave device 100-1, and may track the position (movement, movement, etc.) of the user's head in real-time. The other constituent units included in the slave device 100-1 may be included in the main body of the slave device 100-1.

Referring to FIG. 3B, a slave device 100-2 may be implemented as an earset. A brain wave sensing unit 110-1 of the slave device 100-2 may be located such that it is inserted into a user's ear (for example, inner ear or auris interna), and may sense the user's brain wave in the ear. A speaker unit (not shown) for outputting sound may also be located such that it is inserted into the user's ear together with the brain wave sensing unit 110-1. In addition, an eye tracking unit 130 may be located around the user's eyes and may track the user's eye in real-time. The other constituent units included in the slave device 100-2 may be included in the main body of the slave device 100-2.

In addition, the slave device 100 may be implemented in various form factors to sense the user's gaze position/brain waves, and is not limited to the embodiment shown in the drawing.

FIGS. 4A and 4B are diagrams illustrating an eye-brain (EBI) device according to an exemplary embodiment of the present disclosure. FIG. 5 is a block diagram of the EBI device according to the exemplary embodiment of the present disclosure.

Herein, the EBI device 400 may refer to a device in which the slave device 100 and the host device 150 described above with reference to FIGS. 1 to 3 are integrated into a single device.

Therefore, the EBI device 400 may sense bio-signals by itself and may perform various operations based on the sensing results.

Referring to FIGS. 4A, 4B and 5, the EBI device 400 may be implemented in the form of a wearable device that can be worn on a user's body. The EBI device 400 may include a brain wave sensing unit 500, an eye tracking unit 510, a communication unit 530, a display unit 540 and a processor 520. The units included in the EBI device 400 are identical to those described above with reference to FIG. 2; and, therefore, description will be made focusing on differences.

The brain wave sensing unit 500 may sense a user's brain waves. The brain wave sensing unit 500 may include at least one EEG (Electroencephalogram) sensor and/or MEG (magnetoencephalography) sensor. The brain wave sensing unit 500 may be mounted on the EBI device such that it is located at a part of a user's body (e.g., head) from which the user's brain wave can be measured when the user wears the EBI device, thereby measuring the user's brain wave.

The eye tracking unit 510 may track the user's eye. The eye tracking unit 510 may be mounted in the EBI device 400 such that it is located around the user's eye(s) to track the user's eye (gaze position) in real-time. The eye tracking unit 510 may include a light-emitting element (for example, an infrared LED) that emits light and a camera sensor that receives (or senses) light emitted from the light-emitting element.

The communication unit 530 may conduct communications with an external device using various protocols and may transmit/receive data through the communications. The communication unit 530 may be connected to a network in a wired or wireless manner, and may transmit/receive various signals and/or data.

The display unit 540 may display an image thereon. As used herein, the image may refer to a still image, a moving image, a text, a virtual reality (VR) image, an augmented reality (AR) image or a variety of other visual representations including them that can be displayed on the screen.

The processor 520 may control the brain wave sensing unit 500, the eye tracking unit 510, the communication unit 530, the display unit 540 and the communication unit 530. The processor 520 may control transmission/reception of signals (or data) among the above-described units. The processor 520 may perform various operations in response to the sensing results received from the brain wave sensing unit 500 and/or the eye tracking unit 510.

In the foregoing description, the constituent units included in the EBI device 400 according to the exemplary embodiment of the present disclosure have been described. The EBI device 400 may optionally include some of the constituent units shown in FIG. 5. In addition, the EBI device 400 may further include various units required for the use and operation of the device 400, such as a sensor unit, a memory unit and a power supply unit.

In the following description, the processor 520 and the EBI device 400 may be regarded as the identical element. In addition, in the block diagram shown in FIG. 5 according to the exemplary embodiment of the present disclosure, the blocks represent hardware elements of the EBI devices 400 by logically separating them from one another. Thus, the elements of the EBI device 400 described above may be mounted as a single chip or as a plurality of chips, depending on the design of each device.

As described above, in order to specify the point on the display unit mapped with the coordinates of the user's gaze position in the EBI system, it is necessary to perform calibration to map the coordinates of the user's gaze position with the coordinates of the points on the display unit in advance. In addition, in order to specify a cognitive state mapped with a user's brain wave of a certain frequency, it is also necessary to perform calibration to map the user's brain waves with the cognitive states in advance. In view of the above, there is provided an eye-brain calibration (EBC) interface for calibrating a user's gaze position and brain waves. By using such EBC interface, it is possible to calibrate the user's gaze position and the brain waves simultaneously. It is, however, to be understood that this is merely illustrative. In some exemplary embodiments, the EBI system may calibrate only the brain wave or the eye tracking.

In the following description, the slave/host device and the EBI device will be collectively referred to as an EBI system for convenience of illustration. Therefore, the following description of the EBI system may be applied to a slave device and a host device when the EBI system includes the slave device and the host device, and may be applied to an EBI device when the EBI system includes the EBI device.

FIGS. 6A to 6C are diagrams illustrating embodiments of the EBC interface.

The EBI system according to an exemplary embodiment of the present disclosure may perform calibration of a user's gaze position and brain waves simultaneously through the EBC interface. To this end, the EBI system may provide the user with an EBC interface that induces a particular cognitive state of the user and simultaneously induces the movement of the eyes to a particular point on the screen.

For example, referring to FIG. 6A, an EBI system may sequentially display a plurality of visual objects located at different points as an EBC interface, and may instruct a user to gaze the plurality of visual objects sequentially. In doing so, the EBI system may instruct the user to gaze a particular visual object with a cognitive state of attention, and to gaze another visual object with a cognitive state of rest (or simple gaze/non-attention). To do so, the EBI system may alternately display a plurality of visual objects having different visual effects (e.g., color, size, shape, brightness, flickering, etc.). For example, the EBI system may display red objects and blue visual objects alternately and sequentially, while instructing the user to gaze the red objects in the cognitive state of attention and the blue objects in the cognitive state of rest.

In addition, when the user moves her/his gaze from a visual object to the next visual object, the EBI system may instruct the user to gaze with the cognitive state of search (explore). In doing so, the EBI system may or may not guide (or display) the gaze position path from the visual object to the next visual object.

The EBI system may obtain the coordinates of the user's gaze position associated with a particular visual object, and may obtain the user's brain wave when she/he gazes at the visual object simultaneously. If the EBI system guides the gaze position path between the visual objects, the EBI system may obtain the coordinates of the user's gaze position along the gaze position path and may also obtain the user's brain waves while she/he gazes at the gaze position path. On the other hand, if the EBI system does not guide the gaze position path between the visual objects, the EBI system may obtain the user's brain waves only.

Next, the EBI system may map the coordinates of a visual object on the screen with the obtained coordinates of the user's gaze position. [108] In addition, the EBI system may map a cognitive state of the user that it instructed in association with a visual object with the obtained user's brain wave. Thus, the EBI system provides a method for simultaneously and easily calibrating the gaze position and brain waves through a single interface.

The EBC interface may include a variety of exemplary embodiments in addition to the above-described embodiments. For example, as shown in FIGS. 6A to 6C, the EBC interface may sequentially display a plurality of visual objects in a specific form (e.g., polygon, circle) or in a non-specific form (randomly) one-by-one (or by a predetermined number), or may display alternately visual objects having different visual effects (e.g., color, form, size, shape, flickering, contrast, etc.). Alternatively, the EBC interface may simultaneously display a plurality of visual objects, and then give visual effects to a particular visual object, thereby sequentially indicating the visual object that the user should gaze. In addition, the EBC interface may also instruct the cognitive state of the user through visual effects given to the visual object.

It is known that the frequency of a person's brain wave is synchronized with the frequency of a flickering object she/he watches. Therefore, when a flickering effect is applied as a visual effect to visual objects, the EBC interface may adjust the frequency at which the visual objects flicker to induce the user's brain to a particular cognitive state.

For example, it is known that a frequency of approximately 8 to 12 Hz helps in inducing brain waves into the alpha (α) wave range corresponding to the rest (or search) state. Thus, the EBC interface may give a visual effect such that a visual object flickers at a frequency of approximately 8 to 13 Hz to induce a "rest" state. As a result, the user may be induced to the rest state simply by gazing at the visual object, and the EBI interface may extract the user's brain wave and map it to the cognitive state of rest. It is also known that a frequency of approximately 13 to 30 Hz helps in inducing brain waves into the beta ((3) wave range corresponding to the attention (or wake-up, selection) state. Thus, the EBC interface may give a visual effect such that a visual object flickers at a frequency of approximately 13 to 30 Hz to induce a "attention" state. As a result, the user may be induced to the attention state simply by gazing at the visual object, and the EBI interface may extract the user's brain wave and map it to the cognitive state of attention.

In addition to those described above, the EBC interface can simultaneously calibrate a user's gaze position and brain wave by inducing the user's gaze position at a point on the screen and a particular cognitive state in various ways. In addition, the EBC interface may also obtain a user's iris pattern when calibrating the gaze position. An iris pattern is unique to a user like a fingerprint, and thus it can be useful as user authentication information. As such, once completed the calibration of gaze position/brain waves, the EBI system may use the user's brain wave as control information related to the execution command of the user and may use the user's gaze position as control information about the position of the execution command of the user. For example, if a user gazed at an icon and then paid attention on it, the EBI system can execute a command to run the icon that the user has gazed.

Figure 7:
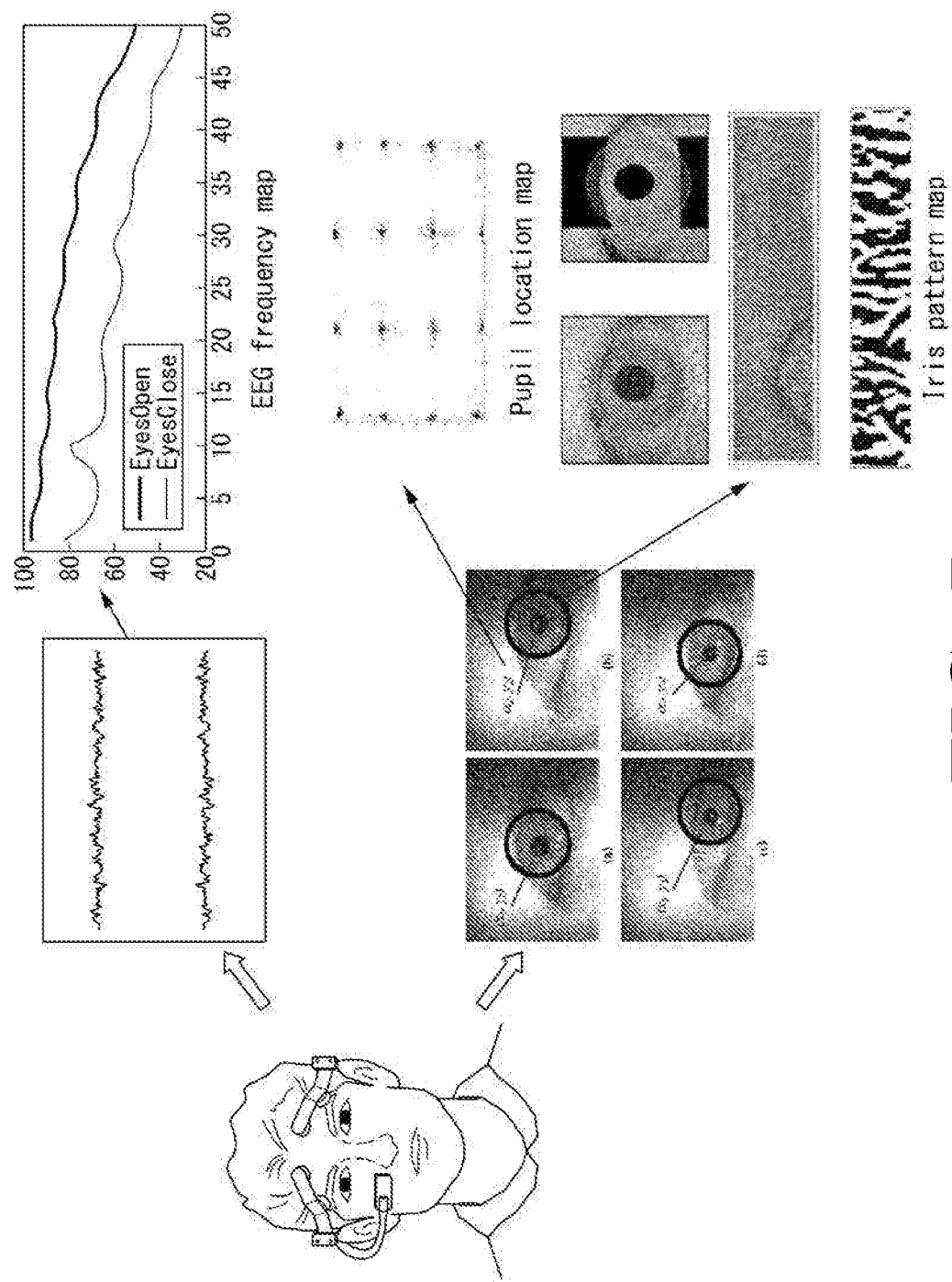
FIG. 7 is a diagram illustrating an example of data obtained by an EBC interface according to an exemplary embodiment of the present disclosure.

FIG. 7 is a diagram illustrating an example of data obtained by an EBC interface according to an exemplary embodiment of the present disclosure.

Referring to FIG. 7, the EBI system may obtain data on the user's gaze position and brain waves simultaneously through the EBC interface. In addition, the EBI system may also obtain data on the iris of the user while providing the EBC interface.

The data thus obtained may be processed by an algorithm. In particular, different users have different brain wave patterns according to cognitive states of attention/non-attention/search, etc. Accordingly, it is necessary to process data through an algorithm in order to more clearly distinguish the brain waves from one another according to each of the cognitive states.

Thus, a method for processing a user's eye tracking will be described with reference to FIG. 8, a method of processing a user's iris will be described with reference to FIG. 9, and a method of processing a user's brain wave will be described with reference to FIGS. 10 to 13.

Figure 8:
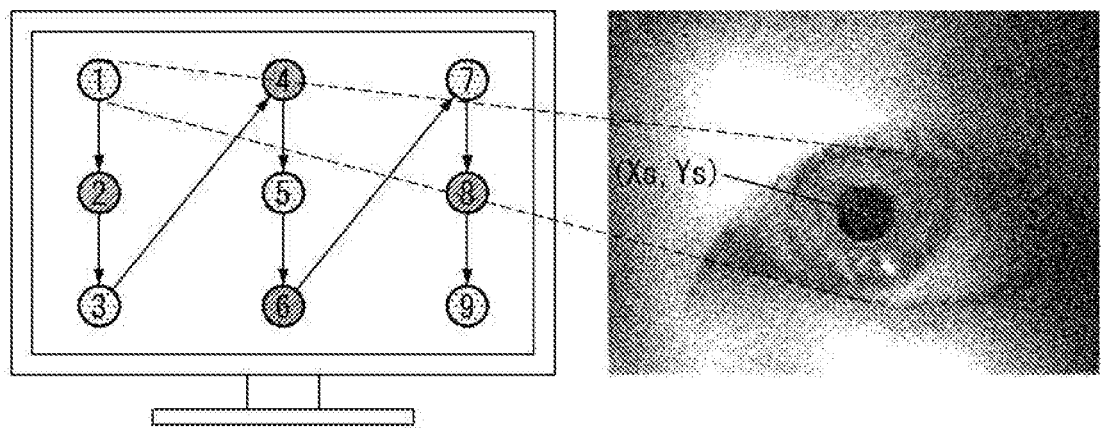
FIG. 8 is a diagram illustrating an EBI system for performing eye tracking calibration according to an exemplary embodiment of the present disclosure.
Figure 9A:
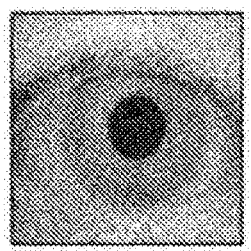
FIGS. 9A to 9D illustrate an EBI system for obtaining a user's iris pattern according to an exemplary embodiment of the present disclosure.
Figure 9B:
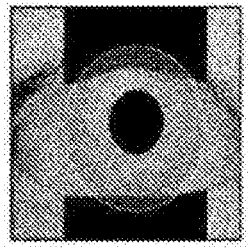
Figure 9C:
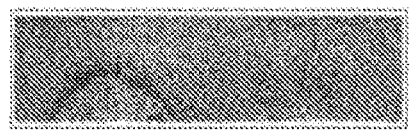
Figure 9D:

FIG. 8 is a diagram illustrating an EBI system for performing eye tracking calibration according to an exemplary embodiment of the present disclosure.

Referring to FIG. 8, assuming that the eye pupil is located at coordinates (Xs, Ys) when the user looks at a point (Xp, Yp) on the screen, the EBI system may estimate the correlation between two spaces using multivariate linear regression or the like.

More specifically, the EBI system may instruct a user to take a look at the point (Xp, Yp) on the screen through the EBC interface. The EBI system may obtain an image by capturing the user's gaze position by using the eye tracking unit and obtain the coordinates (Xs, Ys) of the user's gaze position from the captured image. The coordinates of the user's gaze position may be relative coordinates determined based on the center of the gaze position (or the pupil of the eye). Then, the EBI system may map the point on the screen with the coordinates of the user's gaze position. The EBI system may map the coordinates of the user's gaze position with the point on the screen using Equation 1 below:

Eye-Tracking: $2^{nd}$ Order Linear Regression $$x_p = (a_0 + a_1 x_s + a_2 y_s + a_3 x_s y_s + a_4 x_s^2 + a_5 y_s^2)$$

$$y_p = (a_6 + a_7 x_s + a_8 y_s + a_9 x_s y_s + a_{10} x_s^2 + a_{11} y_s^2)$$  [Equation 1]

In addition to Equation 1 above, other mathematical expressions such as support vector regression and multi-layer perceptron for calibrating the gaze position may be applied.

The EBI system may further utilize data on the user's head position (using the position marker unit, the camera unit and/or the sensor unit) to obtain more accurate user's gaze position coordinates. When a user takes a look at a point, it is natural to move her/his head toward the point as well as the eyes. Based on this, the EBI system may further obtain data on the user's head position to more accurately detect the user's gaze position and may use it as additional data to accurately track the user's eye.

Although the drawing depicts that the eye tracking unit employs the video analysis technique, this is merely illustrative. The eye tracking unit may employ a variety of eye tracking techniques for tracking a user's eye.

The EBI system may further obtain iris pattern data of a user while tracking the user's eye. This will be described below with reference to FIG. 9.

FIGS. 9A to 9D illustrate an EBI system for obtaining a user's iris pattern according to an exemplary embodiment of the present disclosure.

Referring to FIG. 9, the EBI system may not only track a user's eye in real-time through the eye tracking unit but also obtain the user's iris pattern. Like fingerprints, the iris pattern is also unique to the user, and thus the EBI system can utilize the iris pattern as user authentication information. For example, the EBI system may utilize the iris pattern as various user authentication information such as user login authentication information, payment authentication information, and security information.

To this end, the EBI system may set an image of the iris region as an ROI (region of interest) among the infrared images of the user's eye obtained using the eye tracking unit, and may separate the image. Subsequently, the EBI system may divide the separated ROI image into a plurality of images, and then arrange them in one direction. Finally, the EBI system may perform a coding operation for converting the images arranged in one direction into a signal two-dimensional image (for example, a two-dimensional barcode or a QR code), thereby obtaining an iris pattern unique to each user.

The EBI system may obtain an iris pattern using one infrared image. However, in order to obtain a more accurate iris pattern of a user, the EBI system may combine infrared images on eyes of the user looking in different directions to obtain a single iris pattern. The iris pattern of a user becomes less accurate as the area covered due to the eyelid, the angle of the eyes and the light reflection increases. Thus, the EBI system may obtain infrared images on eyes for different directions, obtain an iris pattern from each of the images, and obtain one iris pattern by combining the obtained iris patterns. Therefore, no matter which direction a user gazes, (or even if the pupil is covered by the eyelid), the EBI system can distinguish the iris pattern of the user with high probability.

Figure 10:
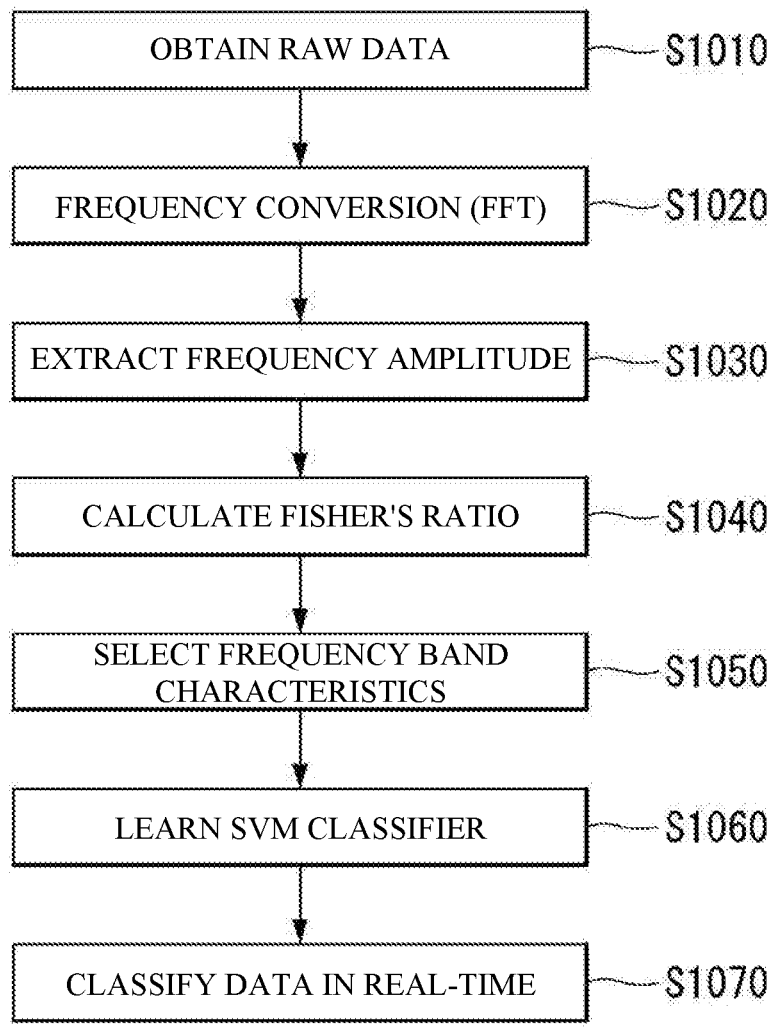
FIG. 10 is a flowchart for illustrating a process of classifying a user's brain waves by an EBI system according to an exemplary embodiment of the present disclosure.

FIG. 10 is a flowchart for illustrating a process of classifying a user's brain waves by an EBI system according to an exemplary embodiment of the present disclosure. FIGS. 11 to 13 depict data obtained by performing some steps of the flowchart.

Referring to FIG. 10, initially, the EBI system may obtain raw data on a user's brain waves using a brain wave sensing unit (step S 1010). In particular, the EBI system may induce various cognitive states of a user (for example, selection/search/attention/rest) through the above-described EBC interface, and may obtain raw data by sensing brain waves in each of the cognitive states.

The EBC interface induced each of the cognitive states of selection/search/attention/rest of the same user in the same environment. As a result, the raw data on the brain waves associated with the cognitive states of selection/search shown in FIG. 11A and the raw data on the brain wave associated with the cognitive states of attention/rest shown in FIG. 12A have been obtained.

Figure 11A:
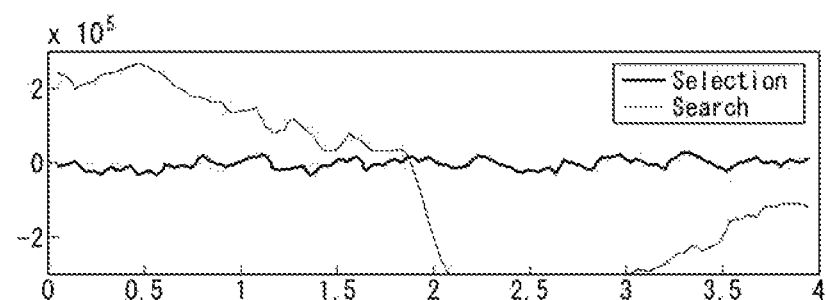
FIGS. 11A-11D, 12A-12D, and 13 depict data obtained by performing some steps of the flowchart.

Referring to FIG. 11A, it could be seen that the brain wave in the search state was more abruptly changed than the brain wave in the selection state. Also, referring to FIG. 12A, it could be seen that the brain wave in the rest state and the brain wave in the attention state cannot be clearly distinguished from each other with naked eyes.

A brain wave is a signal made by synthesizing signals of various sine waves and belongs to a cognitive state depending on its frequency. Therefore, in order to more clearly distinguish the brain waves by the cognitive state, the FFT may be performed on the raw data (step S1020). In doing so, Equation 2 below may be used:

$$X_k = \sum_{n=0}^{N-1} x_n e^{-i2\pi k \frac{n}{N}} \quad k = 0, \ldots, N-1 \quad \text{[Equation 2]}$$

Figure 11B:
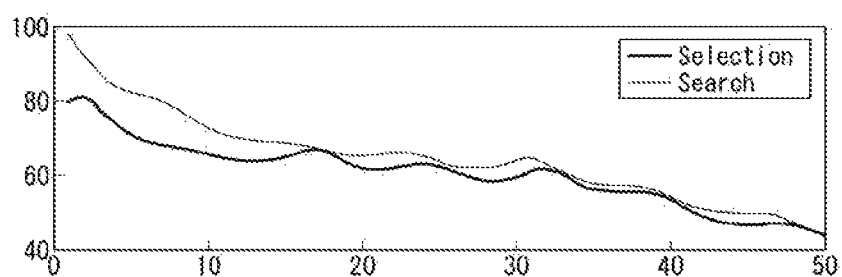
Figure 12A:
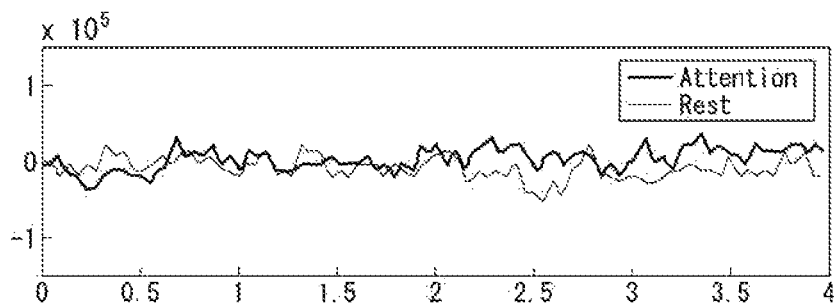
Figure 12B:
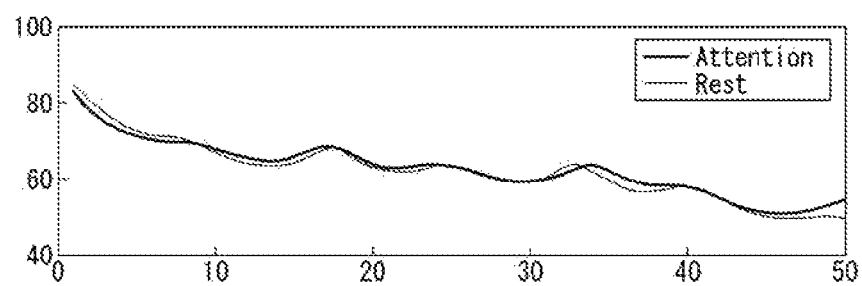
Figure 13:
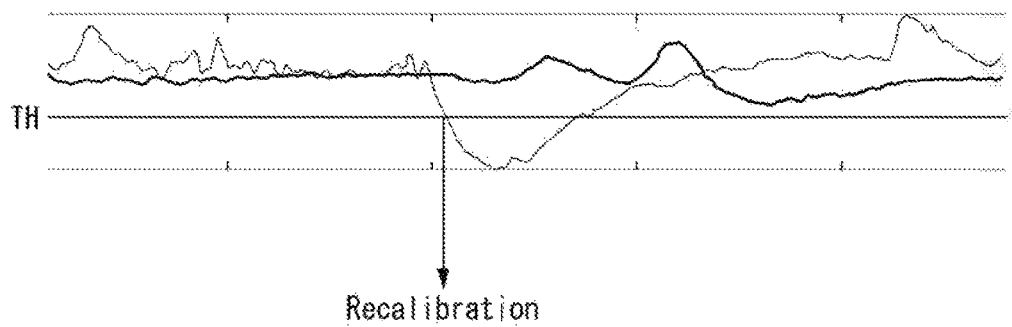

FIGS. 11B and 12B are graphs obtained by performing the FFT on the raw data. Referring to FIG. 11B, it could be seen that the brain waves in the search and selection states exhibited a large difference in the frequency band of approximately 0 to 10 Hz. Referring to FIG. 12B, it could be seen that the brain waves in the attention and rest states exhibited a large difference in the frequency band of approximately 10 to 20 Hz.

The EBI system may extract a frequency amplitude for each frequency band of brain waves from the sample data converted into the frequency domain (step S1030). The extractable frequency bands may be largely divided into four bands, which are δ wave (0 to 4 Hz), θ wave (4 to 8 Hz), α-wave (8 to 13 Hz) and β-wave (13 to 30 Hz). The α-wave and β-wave may be further divided into a low α wave (8 to 10 Hz), a high α-wave (10 to 13 Hz), a low β-wave (13 to 20 Hz) and a high β-wave (20 to 30 Hz). The frequency amplitude may be extracted from each of the divided bands, and the frequency amplitude may be applied to the algorithm for extracting the characteristics of the brain waves.

Different users have different patterns of brain waves for the same stimulus. Therefore, it is necessary to calibrate the brain waves for each user in order to process brain wave data accurately for each user. To this end, an algorithm for extracting frequency characteristics of brain waves according to cognitive states for each user (or an algorithm for setting a criterion for classifying the cognitive states of brain waves) may be applied. In this exemplary embodiment, Fisher's ratio was used. Fisher's ratio is a criterion for measuring the discriminative power between data groups, and may be calculated by Equation 3 below:

$$\text{Fisher's Ratio} = \frac{(m_1 - m_2)^2}{v_1 + v_2} \quad \text{[Equation 3]}$$

In Equation 3, m1 denotes the average of one of the two data groups, m2 denotes the average of the other one of the data groups, v1 denotes the variance of one data group, and v2 denotes the variance of the other one of the data groups. The averages and variances may be calculated using the frequency amplitudes extracted for each frequency band. Therefore, m1 and v1 may be the average and variance of the frequency amplitude of the raw data in the search (or attention) state, respectively, after the raw data has been subjected to the FFT. The m2 and v2 may be the average and variance of the frequency amplitude of the raw data in the attention (or rest) state, respectively, after the raw data has been subjected to the FFT. The Fisher's ratio of the frequency coefficients according to the cognitive states may be obtained by Equation 3 (step S1040). Fisher's Ratio may be used to measure the discriminative power between two standard distributions. More specifically, by searching a frequency band in which the frequency amplitude in a specific cognitive state (for example, selection/attention/rest/search, etc.) of the user is maximized for the frequency bands by using Fisher's ratio, it is possible to find the optimal frequency band for distinguishing a particular cognitive state for each user.

Fisher's ratio of brain waves for each of the frequency bands is compared with another, and two frequency bands of the brain waves having the highest Fisher's ratios (the highest and the second highest Fisher's ratios) may be selected as characteristic frequency bands for distinguishing between cognitive states (step S1050). By using the Fisher's ratios, two characteristic frequency bands that have a significant impact on each cognitive state may be extracted. A larger Fisher's ratio is more accurate to distinguish between the cognitive states.

Figure 11C:
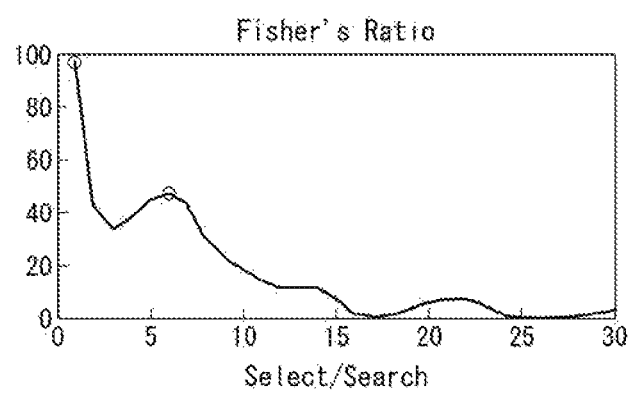
Figure 12C:
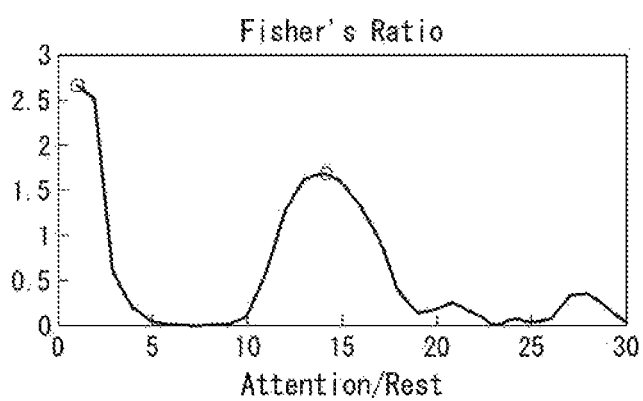

FIG. 11C shows the Fisher's ratio calculated from the brain wave in the selection/search state. FIG. 12C shows the Fisher's ratio calculated from the brain wave in the attention/rest state. Referring to FIG. 11C, the selection/search state exhibited a characteristic that they are distinguished in the frequency band of approximately 0 to 5 Hz and the frequency band of approximately 5 to 10 Hz. Referring to FIG. 12C, the attention/rest state exhibited a characteristic that they are distinguished in the frequency band of approximately 0 to 5 Hz and the frequency band of approximately 10 to 20 Hz.

Figure 11D:
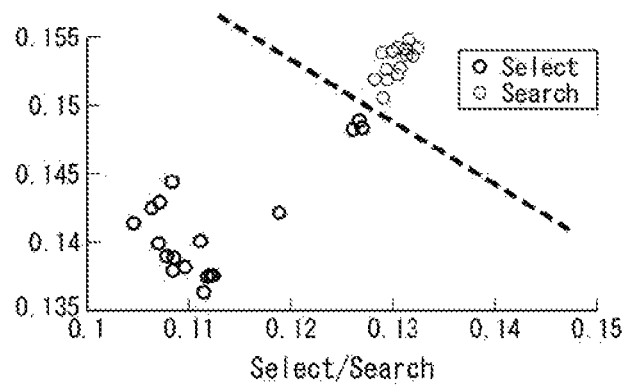
Figure 12D:
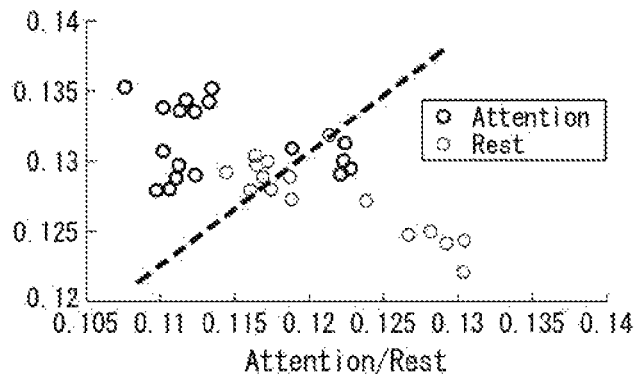

FIGS. 11D and 12D are graphs showing the amplitudes of the characteristic frequency bands extracted by using the Fisher's ratios in the selection/search/attention/rest states in a two-dimensional space. Referring to FIGS. 11D and 12D, it could be seen that data items in the same cognitive state are gathered at particular positions.

As such, once the characteristic frequency bands for distinguishing between the cognitive states are extracted by using the Fisher's ratio, the calibration of the brain waves is completed.

Next, the EBI system may apply a classification model that can determine to which group newly obtained data belongs (step S1060). In other words, the EBI system may apply a classification model that can determine to which cognitive state a newly obtained brain wave belongs. For example, the EBI system may apply support vector machine (SVM) as the classification model. It is known that SVM exhibits better generalization ability and performance than other classification models. The EBI system may distinguish (or classify) newly obtained brain wave data in real-time through the SVM by the cognitive state based on the characteristics previously acquired using the Fisher's ratio (step S1070).

As such, by using the Fisher's ratio and SVM techniques, which extract the characteristics of the frequency bands, it was possible to distinguish between cognitive states of the brain waves with an accuracy of approximately 80% or higher. So far, there was no specified standard or and method for calibrating a user's brain waves, devices were controlled only with the user's brain waves, which exhibited a low accuracy. In contrast, cognitive states of a user's brain wave can be more accurately distinguished by the method for calibrating according to an exemplary embodiment of the present disclosure, and the user can accurately control the device as intended only with the brain waves.

Each step of the flowchart of FIG. 10 may be performed by at least one device included in the EBI system. For example, if the EBI system includes a single EBI device, the steps of the flowchart of FIG. 10 may be performed by the EBI device. Or, if the EBI system includes a slave device and a host device, some of the steps of the flowchart of FIG. 10 may be performed by the slave device while the other steps m performed by the host device.

FIG. 13 is a diagram illustrating an example of a recalibration method according to an exemplary embodiment of the present disclosure.

Upon completion of the calibration through the EBC interface, the EBI system can map/classify the newly obtained data on gaze position and brain wave based on the calibration results, and perform various commands corresponding to the mapping/classification status. For example, the EBI system may map a user's gaze position with an icon on the screen based on the calibration results. Further, when the EBI system further obtains brain wave data classified as the attention (or selection) state while the user is looking at the icon, the EBI system may perform a command to select and execute the icon.

That is, the EBI system performs mapping/classification of newly obtained data based on the calibration results, and executes a command corresponding to the mapped/classified data. However, even after the calibration is completed, the current environment may be changed from the environment at the time of calibration, or the user or the user environment may be changed, such that the accuracy of the calibration results may be lowered. When this happens, the EBI system is required to perform calibration again (recalibration). [155] Trigger recalibration of the EBI system may include various exemplary embodiments.

As an exemplary embodiment, the recalibration of the EBI system may be triggered directly by a user. For example, an EBI system may perform recalibration upon receiving a user input to instruct to perform recalibration. The user input may include various types of inputs such as voice, touch, gesture, motion and operation of the user.

In another exemplary embodiment, referring to FIG. 13, the recalibration of the EBI system may be triggered automatically by measuring a user's stress index. The user's stress index may be increased if the device fails to operate (malfunctioning) according to the brain wave and gaze position as intended by the user. Therefore, if the user's stress index is out of a predetermined threshold (TH) range, the EBI system may determine that recalibration is necessary and may perform the recalibration.

It is known that beta waves and gamma waves among users' brain waves are known to be related to the stress index. Thus, the EBI system may measure in real-time gamma and beta waves of the user's brain waves and may perform recalibration when a wave is out of the predetermined threshold range.

In addition to the gamma and beta waves, the EBI system may measure in real-time biological signals known to be related with the stress index, such as heart rate and blood pressure, and may trigger recalibration based on the measurements.

The EBI system provides the user with the EBC interface again for performing the recalibration.

Figure 14:
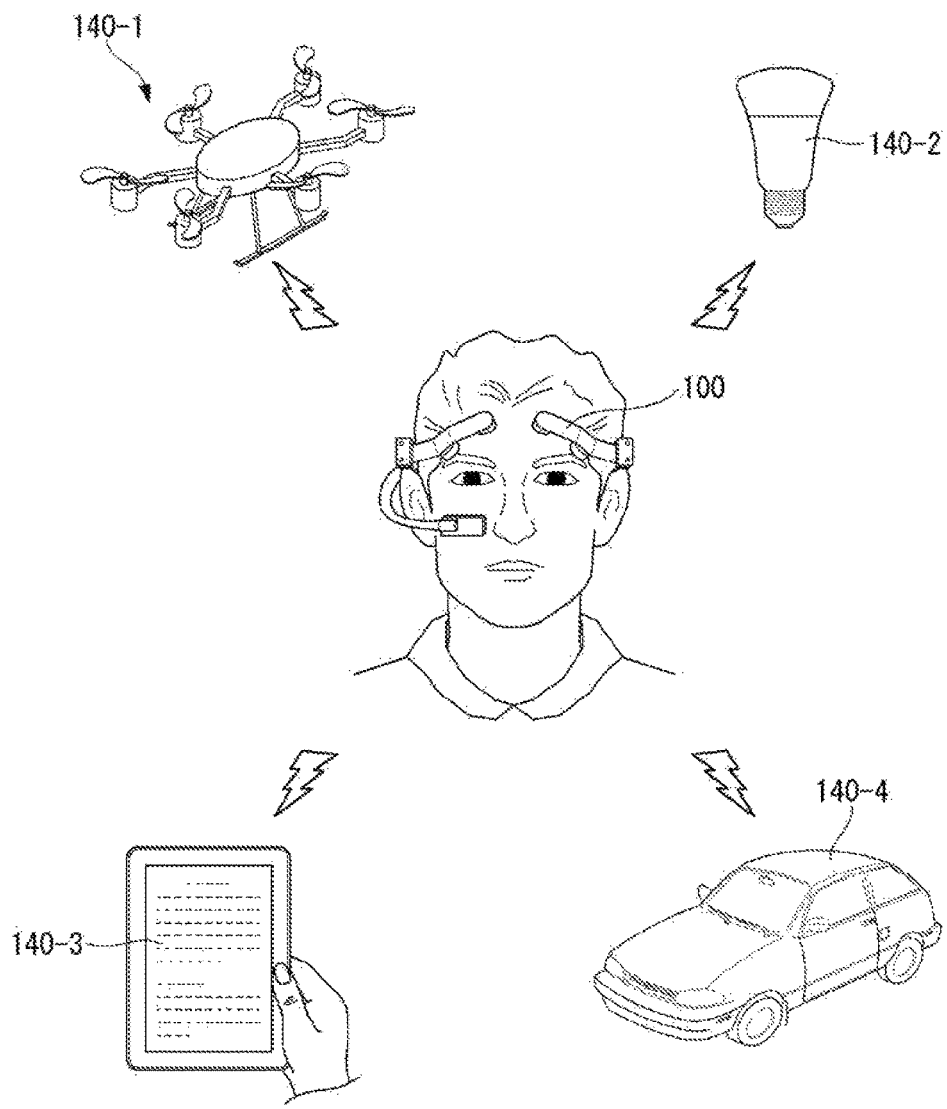
FIG. 14 is a diagram illustrating various applications of an EBI system according to an exemplary embodiment of the present disclosure.

FIG. 14 is a diagram illustrating various applications of an EBI system according to an exemplary embodiment of the present disclosure.

Referring to FIG. 14, the EBI system may find applications in a variety of technical fields such as drone control technology, home network technology, educational technology, portable device technology, vehicle control technology and entertainment field.

When the EBI system is applied to the drone control technology, the host device may be a drone 140-1 and the slave device may be a wearable device 100. The user controls the drone with the brain waves and the gaze position while wearing the slave device.

For example, when the wearable device 100 is a wearable headset, the user can control the movement of the drone 140-1 through the head position. When the user moves her/his head forward/backward/left/right, the drone may also move forward/backward/left/right in response to the movement of the user's head. In addition, when the user wearing the wearable device 100 pays attention on the drone 140-1, the moving speed of the drone 140-1 may increase. When the user rests while watching the drone 140-1, the drone 140-1 may stay where it is. In addition those described above, the drone 140-1 may operate in response to a variety of bio-signals of the user.

The EBI system may be applied to the vehicle control technology similarly to the drone control technology. For example, the EBI system may be applied to the technology for controlling a variety of vehicles such as automobiles, airplanes and bicycles. In this case, a vehicle 140-4 may be a host device, and a wearable device 100 worn on a user may be a slave device.

When the EBI system is applied to the home network technology, a variety of home devices 140-2 located at home may be host devices, and a wearable device 140-4 to be worn on a user may be a slave device. In this case, the user wearing the wearable device 140-4 may take a look at a home device 140-2 to issue a command through a brain wave, thereby controlling the home devices conveniently. For example, if the user wearing the wearable device 100 takes a look at a bulb 140-2 and keeps the "attention" state, the bulb 140-2 may be turned on or off.

When the EBI system is applied to the educational technology, a variety of educational devices 140-3 may be host devices, and a wearable device 100 to be worn on a user may be a slave device. As the EBI system can measure a user's attention, it can track the degree of concentration of the user in real-time. The EBI system may recommend the user study again the part which the user studied at a low degree of concentration, thereby helping in improving the learning efficiency.

In addition to the above-described applications, the EBI system can be applied to various technical fields. In particular, the exemplary embodiments of the present disclosure may be applied to various fields to which a control technique using a user's bio-signal can be applied, and is not limited to the above-described embodiments.

In some applications that require only one of the brain waves and the gaze position as a control signal, the EBI system may perform calibration only on the required one of the brain waves and gaze position. That is, in some exemplary embodiments, the EBI system may calibrate brain waves and gaze position simultaneously or only one of the brain wave and the gaze position.

Figure 15:
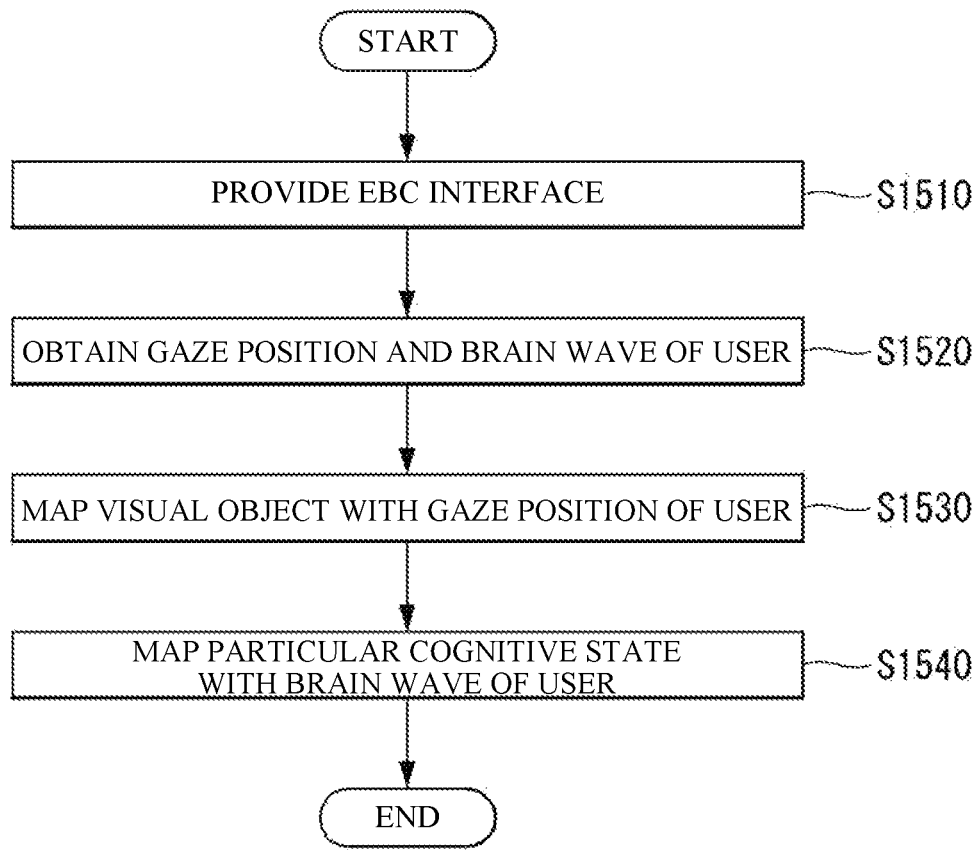
FIG. 15 is a flowchart for illustrating a method for controlling an EBI system according to an exemplary embodiment of the present disclosure.

FIG. 15 is a flowchart for illustrating a method for controlling an EBI system according to an exemplary embodiment of the present disclosure. In describing the flowchart, the description of the above-described embodiments may be equally applied. Therefore, the redundant description will be omitted.

Initially, the EBI system may provide the EBC interface (step S1510). More specifically, the EBI system may provide the EBC interface for calibrating the user's gaze position and brain waves simultaneously. The EBC interface may include at least one visual object, and may instruct the user to gaze a visual object in a particular cognitive state. The EBC interface to be provided to users may have a variety of exemplary embodiments, as described above with respect to FIG. 6.

Subsequently, the EBI system may obtain the user's gaze position and brain waves (step S1520). More specifically, the EBI system may obtain the user's gaze position and brain waves on the EBC interface using the brain wave sensing unit and the eye tracking unit.

Subsequently, the EBI system may map the visual object provided by the EBC interface with the user's gaze position (step S1530). In doing so, the EBI system may map the coordinates of the visual object position with the coordinates of the user's gaze position. The EBI system may map the position of the visual object and the position of the user's gaze position through the multivariate linear regression and the like, as described above with respect to FIG. 8.

Finally, the EBI system may map the user's brain waves with the particular cognitive state instructed by the EBC interface (step S1540). In this case, the EBI system may obtain raw data for the particular cognitive state and process the obtained data through a predetermined algorithm, to thereby set a criterion for classifying the cognitive state. The example of the predetermined algorithm for setting the criterion has been described above with reference to FIG. 10.

Steps S1530 and S1540 of the flowchart may be switched, and a new step may be added or some steps may be eliminated in some exemplary embodiments.

Although not illustrated in the flowchart, the EBI system may obtain an iris image from the user's eye, and may code the obtained iris image to use it as user authentication information. This has been described above with reference to FIG. 9.

Each step of the flowchart may be performed by at least one device included in the EBI system. If the EBI system includes a single EBI device, the steps illustrated in the flowchart may be performed by the single EBI device. If the EBI system includes a slave device and a host device, some of the steps illustrated in the flowchart may be performed by the slave device and the other of the steps may be performed by the host device.

For example, steps S1510, S1530 and S1540 may be performed by the host device, and step S1520 may be performed by the slave device. In this case, the host device may receive (or request and receive) the data obtained by performing the step S1520 from the slave device, and may perform steps S1530 and S1540 based on the received data.

In addition to the slave device or the host device described above, the subjects that perform each step of the flowchart may be changed depending on the number of devices included in the EBI system, constituent units of each device, design purpose, etc. To perform the steps, signals may be transmitted/received between the devices. Accordingly, when the EBI system includes a plurality of devices, it is to be understood that the data required to perform a certain step is included in the signals transmitted/received between the devices.

Although exemplary embodiments have been described throughout several views, the exemplary embodiments may be combined to implement a new exemplary embodiment. The configuration and method applied the display device are not limited to those described above. Some or all of the exemplary embodiments may be selectively combined to make a variety of modifications to the exemplary embodiments.

Although the exemplary embodiments of the present disclosure have been disclosed for illustrative purposes, those skilled in the art will appreciate that various modifications, additions and substitutions are possible, without departing from the scope and spirit of the claims. Accordingly, such modifications, additions and substitutions should also be understood as falling within the scope of the present disclosure.

DESCRIPTION OF EMBODIMENTS

Various embodiments have been described in the best mode for carrying out the invention.

INDUSTRIAL APPLICABILITY

Exemplary embodiments of the present disclosure can be used in various control systems using a user's brain waves and eye tracking.

What is claimed is:

1. A method for calibrating eye tracking and brain waves, the method comprising:
providing sequentially and/or alternately a first visual object with a first cognitive state and a second visual object with a second cognitive state;
obtaining gaze positions and brain waves of user on the first visual object and the second visual object;
calibrating the gaze positions with the brain waves, and the first and second cognitive states with the gaze positions and brain waves,
wherein the first cognitive state is a cognitive state of attention, and the second cognitive state is a cognitive state of rest.

2. The method of claim 1, further comprising:
adjusting flickering frequencies of the first visual object and the second visual object.

3. The method of claim 2, further comprising:
obtaining first raw data on a brain wave in the first cognitive state, and second raw data on a brain wave in the second cognitive state;
converting frequencies of the first raw data and the second raw data; and
setting a criterion for classifying the first and second cognitive states based on the frequency characteristics of the frequency-converted first raw data and the second raw data,
wherein the setting the criterion comprises:
extracting a frequency amplitude for each of frequency bands in a predetermined range from the frequency-converted first raw data and second raw data;
obtaining a Fisher's ratio for each of the frequency bands using the extracted frequency amplitude;
selecting a first frequency band having a highest Fisher's ratio and a second frequency band having a second highest Fisher's ratio; and
setting the first and second frequency bands as the criteria for classifying the first and second cognitive states.

4. The method of claim 3, wherein the Fisher's ratio is calculated based on an average and a variance of the frequency amplitudes in the frequency-converted first raw data and an average and a variance of the frequency amplitudes in the frequency-converted second raw data.

5. The method of claim 2, wherein the frequency band in the predetermined range corresponds to δ-wave band, θ-wave band, α-wave band or β-wave band of a brain wave.

6. The method of claim 2, wherein the adjusting a flickering frequencies comprises:
adjusting the flickering frequencies of the first visual object and the second visual object to approximately 8 to 13 Hz to induce the brain wave to an alpha wave range, or adjusting the flickering frequencies of the first visual object and the second visual object to approximately 13 to 30 Hz to induce the brain wave to a beta wave range.

7. The method of claim 1, further comprising:
obtaining an iris image from the user's eye; and coding the iris image.

8. The method of claim 7, wherein the coding the iris image comprises:
dividing the obtained iris image into a plurality of images;
arranging the plurality of images in one direction; and
converting the images arranged in the one direction into a single two-dimensional image.

9. A host device controlled based on eye tracking and brain waves, comprising:
a display configured to display an image; and
a processor configured to
control the display and provide a first visual object with a first cognitive state and a second visual object with a second cognitive state,
request and receive gaze positions and brain waves of a user on the first visual object and the second visual object,
and calibrate the gaze positions with the brain waves and the first and second cognitive states with the gaze positions and brain waves,
wherein the first cognitive state is a cognitive state of attention, and the second cognitive state is a cognitive state of rest.

10. The host device of claim 9, wherein the processor is further configured to
adjust a flickering frequencies of the first visual object and the second visual object;
obtain first raw data on a brain wave in the first cognitive state, and second raw data on a brain wave in the second cognitive state,
convert frequencies of the first raw data and the second raw data,
extract a frequency amplitude for each of frequency bands in a predetermined range from the frequency-converted first raw data and second raw data,
obtain a Fisher's ratio for each of the frequency bands using the extracted frequency amplitude,
select a first frequency band having a highest Fisher's ratio and a second frequency band having a second highest Fisher's ratio, and
set the first and second frequency bands as the criteria for classifying the first and second cognitive states.

11. The host device of claim 10, wherein the processor is further configured to obtain the brain waves of the user in real-time and classifies the brain waves of the user obtained in real-time according to the criteria in real-time.

* * * * *